US00PP08085P

United States Patent [19]

Zaiger et al.

[11] Patent Number: Plant 8,085

[45] Date of Patent: Jan. 5, 1993

[54] PEACH TREE "SNOW GIANT"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95351

[21] Appl. No.: 750,255

[22] Filed: Aug. 27, 1991

[51] Int. Cl.[5] ..... A01H 5/00

[52] U.S. Cl. ..... Plt./42.1

[58] Field of Search ..... Plt./42.1

*Primary Examiner*—James R. Feyrer

[57] ABSTRACT

The new and distinct variety relates to a peach tree which has the following unique combination of desirable features:

1. Production of fruit with excellent flavor and eating quality.
2. Heavy and regular production of fruit with large size.
3. Vigorous, upright growth.
4. Fruit with firm white flesh, good storage and shipping quality.
5. Production of fruit with a high degree of attractive red skin color.
6. Fruit ripening in the late maturity season.

1 Drawing Sheet

ORIGIN OF THE VARIETY

The present variety of peach tree was originated by us in our experimental orchard located near Modesto, Calif., as a first generation cross between two selected seedlings with the field identification numbers 18EA213 and 51GA205. The female parent 18EA213 originated from a second generation cross between a nectarine seedling of unknown parentage and Royal Gold Peach (U.S. Plant Pat. No. 2,663). The pollen parent originated from a first generation cross between a selected seedling from an open pollinated O'Henry Peach (U.S. Plant Pat. No. 2,964) crossed with a selected seedling originating from a cross between an open pollinated May Grand Nectarine (U.S. Plant Pat. No. 2,794) seedling crossed with Sam Houston Peach (non-patented). (Royal Gold Peach is classified as a yellow flesh peach, it originated as a bud mutation from the white flesh peach Spring Time (U.S. Plant Pat. No. 1,268) and carries a factor for white flesh). The present variety was selected from a large group of seedlings which were grown and maintained under careful observation during which time we recognized its desirable characteristics described above and selected the variety for asexual reproduction and commercialization.

ASEXUAL REPRODUCTION OF THE VARIETY

The present variety of peach tree was asexually propagated by budding, as performed by us in our experimental orchard located near Modesto, Calif., and shows that all characteristics run true to the original tree and are established and transmitted through succeeding propagations.

SUMMARY OF THE VARIETY

A new and distinct variety of peach tree which is of large size, with vigorous upright growth and being a productive and regular bearer of large, white flesh, freestone fruit with excellent flavor and eating quality. The fruit is further characterized by relatively uniform size throughout the tree, having firm white flesh with good storage and shipping quality and having a high degree of attractive red skin color; and in comparison to Giant Babcock Peach (U.S. Plant Pat. No. 1,353), the new variety has the ability to produce a greater number of large, uniform sized fruit, with a higher degree of attractive red skin color and ripening approximately one month later.

PHOTOGRAPHS OF THE VARIETY

The accompanying photographic illustrations show typical specimens of the foliage and fruit of our new peach variety with the upper and lower surface of the leaves being shown and the exterior and a cross sectional view of the fruit divided in the suture plane to reveal flesh coloration and showing a stone remaining in place. The photographs were taken shortly after being picked at maturity (firm ripe) and the colors are as nearly true as reasonably possible in a color representation of this type.

DESCRIPTION OF THE VARIETY

The following is a detailed botanical description of the present variety of peach tree, its flowers, foliage and fruit as based on observations of specimens grown near Modesto, Calif., with color terminology (except those in common terms) in accordance with Reinhold Color Atlas by A. Kornerup and J. H. Wanscher.

Tree:

*Size.*—Large.
*Density.*—Medium dense.
*Vigor.*—Vigorous.
*Form.*—Upright.
*Productivity.*—Productive.
*Bearer.*—Regular.

Trunk:

*Size.*—Medium stocky.
*Surface.*—Medium shaggy.
*Color.*—Brown to grayish brown (5-E-4) to (5-E-6).

Branches:

*Size.*—Medium to large.
*Texture.*—Varies from smooth to medium rough.
*Lenticels.*—Medium size. Medium number.
*Color.*13 Light brown to brown (5-D-4) to (5-D-6).

Leaves:

*Size.*—Large. Average length — $6\frac{3}{4}''$. Average width — $1\frac{1}{4}''$.

*Form.*—Lanceolate.

*Margin.*—Crenate.

*Texture.*—Smooth to slightly rugose on older leaves.

*Petiole.*—Medium length. Medium thickness.

*Glands.*—Globose. Medium size. Number varies from 0 to 3. Average number 2. Positioned on base of leaf blade and upper portion of petiole, usually alternate.

*Color.*—Upper surface — green to dark green (27-F-6) to (27-F-8). Lower surface — green to grayish green (27-E-4) to (27-E-6).

Flower buds:

*Size.*—Large.

*Form.*—Plump.

*Pubescence.*—Pubescent.

Flowers:

*Size.*—Large — showy.

*Blooming period.*—Mar. 2, 1990 to Mar. 8, 1990. Varies slightly due to climatic conditions.

*Pollen.*—Present — self-fertile.

*Color.*—Pink.

Fruit:

*Maturity when described.*—Firm ripe.

*Date of first picking.*—Aug. 7, 1990.

Date of last picking.13 Aug. 13, 1990.

*Size.*—Large Average diameter axially — $3\frac{1}{4}''$ to $3\frac{3}{8}''$. Average transversely in suture plane—3" to $3\frac{1}{8}''$.

*Form.*—Nearly globose — varies from globose to slightly elongated.

*Suture.*—Shallow, extends from base to apex.

*Surface.*—Rounded to slightly recessed.

*Apex.*—Nearly rounded, only very slight apical point.

*Base.*—Retuse.

*Cavity.*—Rounded to slightly elongated in suture plane. Average depth — $\frac{1}{2}''$. Average breadth — 1".

Skin:

*Thickness.*—Medium.

*Texture.*—Medium, tenacious to flesh.

*Tendency to crack.*—None.

*Down.*—Moderate. Medium length.

*Color.*—White to yellowish white ground color (4-A-1) to (4-A-2). Overspread with red to cock's comb red (10-A-7) to (10-B-8).

Flesh:

*Texture.*—Firm.

*Ripens.*—Evenly.

*Fibers.*—Few, small and tender.

*Amygdalin.*—Undetected.

*Flavor.*—Excellent — mild, sub-acid, sweet.

*Juice.*—Moderate.

*Aroma.*—Moderate.

*Eating quality.*—Excellent.

*Color.*—White to slightly pinkish white (8-A-1) to (8-A-2). Pit cavity is red to madder red (10-A-7) to (10-B-7) with slight bleeding of red color into flesh around pit cavity.

Stone:

*Type.*—Freestone.

*Size.*—Large. Average length — $1\frac{3}{8}''$. Average breadth — 1". Average thickness — $\frac{3}{4}''$.

*Form.*—Oval to ovoid.

*Base.*—Mostly rounded, varies from rounded to straight.

*Apex.*—Usually acuminate, some sides being more pronounced and extending nearer to point of apex.

*Sides.*—Equal to unequal.

*Surface.*—Furrowed toward apex, pitted toward base. Pit cavity varies from elongated to round.

*Tendency to split.*—Very slight.

*Color.*—Brown to reddish brown (9-D-4) to (9-D-7).

Use:

*Markets.*—local and long distance. Dessert.

Keeping quality: Good.

Shipping quality: Good.

The present variety, its flowers and fruit herein described may vary in slight detail due to climatic conditions, soil type and cultural practices under which the variety may be grown; the present description is that of the variety grown under the ecological conditions prevailing near Modesto, Calif.

We claim:

1. A new and distinct variety of peach tree, substantially as illustrated and described, characterized by its large size, virgorous, upright growth and being a productive and regular bearer of large, white flesh fruit with excellent flavor and eating quality; the present variety is further characterized in comparison to the white flesh peach Giant Babcock (U.S. Plant Pat. No. 1,353) as having the ability to produce a greater number of large, uniform sized fruit with a higher degree of attractive red skin color and the fruit maturing approximately one month later.

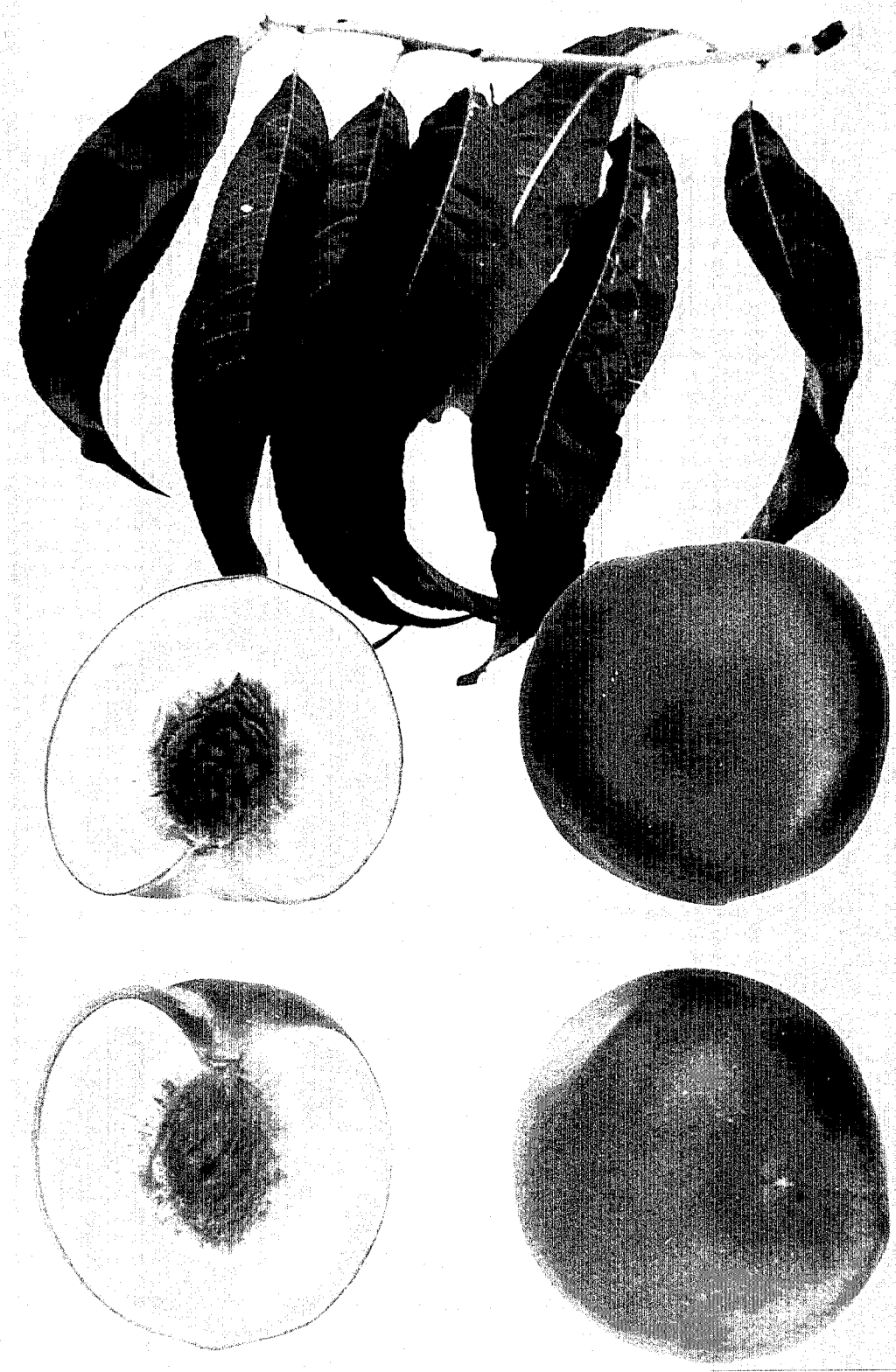

* * * * *